(12) United States Patent
McMillan et al.

(10) Patent No.: US 10,928,372 B2
(45) Date of Patent: Feb. 23, 2021

(54) ELECTRONIC DEVICE

(71) Applicant: AMS SENSORS UK LIMITED, Cambridge (GB)

(72) Inventors: Douglas James McMillan, Cambridge (GB); Clinton Sean Dixon, Cambridge (GB); Simon Jonathan Stacey, Ely (GB)

(73) Assignee: AMS SENSORS UK LIMITED, Cambridgeshire (GB)

( * ) Notice: Subject to any disclaimer, the term of this patent is extended or adjusted under 35 U.S.C. 154(b) by 446 days.

(21) Appl. No.: 15/010,167

(22) Filed: Jan. 29, 2016

(65) Prior Publication Data
US 2017/0219544 A1 Aug. 3, 2017

(51) Int. Cl.
*G01N 33/00* (2006.01)
*G01N 27/04* (2006.01)
*G08B 21/12* (2006.01)
*G08B 29/16* (2006.01)
*G08B 25/08* (2006.01)

(52) U.S. Cl.
CPC ....... *G01N 33/0073* (2013.01); *G01N 27/045* (2013.01); *G01N 33/0063* (2013.01); *G01N 33/0065* (2013.01); *G08B 21/12* (2013.01); *G08B 25/08* (2013.01); *G08B 29/16* (2013.01)

(58) Field of Classification Search
CPC .......... G01N 33/0073; G01N 33/0062; G01N 27/045; G01N 30/8696; G01F 1/26
See application file for complete search history.

(56) References Cited

U.S. PATENT DOCUMENTS

| 5,088,314 | A | 2/1992 | Takashi | |
|---|---|---|---|---|
| 8,943,352 | B1 * | 1/2015 | Warneke | G06F 1/3234 713/500 |
| 2006/0114113 | A1 | 6/2006 | Yokosawa | |
| 2014/0216129 | A1 | 8/2014 | Schmidlin | |

FOREIGN PATENT DOCUMENTS

JP  H0636159 A  2/1994

OTHER PUBLICATIONS

International Search Report and Written Opinion from corresponding International Application No. PCT/GB2017/050225, dated Apr. 12, 2017.

* cited by examiner

*Primary Examiner* — Leslie J Evanisko
*Assistant Examiner* — Leo T Hinze
(74) *Attorney, Agent, or Firm* — Tucker Ellis LLP

(57) ABSTRACT

We disclose herein an electronic device comprising: a state machine for receiving an output signal from a sensor; a comparator operatively coupled with the state machine; and a first processor operatively coupled with the comparator. The state machine is configured to receive the output signal from the at least one sensor to obtain sensor measurement data and configured to pass the obtained sensor measurement data to the comparator. The comparator is configured to process the obtained sensor measurement data into first processed sensor data, and configured to compare the first processed sensor data with a first predetermined threshold limit. The comparator is configured to inform the first processor about the obtained sensor measurement data if the first processed sensor data exceed the first predetermined threshold limit.

38 Claims, 3 Drawing Sheets

ELECTRONIC DEVICE

FIELD OF THE INVENTION

This invention relates to an electronic device, particularly but not exclusively, relates to a portable electronic device for optimised sensor management and for escalation processing for low power system solution.

BACKGROUND OF THE INVENTION

In a system that desires sensor data there is typically a Host or Applications Processor that has access to many systems resources which carry a significant overhead in power requirements.

Instances of a single processor stage in addition to the Host or Application Processor have been used, for example, multi core processors or separate "sensor hub" architectures. A typical sensor hub architecture is shown in FIG. 1 according to prior art. The 'Sensor Hub' uses a low power microprocessor to manage multiple Sensors and processing of multiple steps such as sensor control and measurement, basic processing of the measurement data. The sensor hub is a low power microprocessor which is capable of consuming a reasonable amount of power. In the prior art arrangement of FIG. 1, since all the processing is performed by the single processor, the power management is not optimised.

SUMMARY

Embodiments of the invention make different resources available for different levels of control and processing. Higher levels of processing are typically capable of the actions performed by the lower levels, but they are not able to perform the processing at the low power budgets that the lower processing levels can achieve due to the overheads and resources that are also involved.

One of the most common applications of Gas Sensing is 'always on' monitoring for levels that may be considered dangerous or otherwise trigger an alarm condition.

Where these applications are battery powered (either main power or back-up) the power drain on the battery should be kept to a minimum to ensure that the sensing and ability to raise an alarm can be maintained for the longest time.

Data from Gas Sensors generally requires some processing to determine the presence or concentration of the gas being monitored.

Embodiments of the invention involve using low power processing where possible to reduce (minimise) the power required in the detection process and this can take the form of multiple processing solutions, each capable of different levels of processing and requiring different amounts of power to do that processing; the lowest power solution for a given level of processing being chosen at any time.

We disclose herein a portable electronic device comprising electronic components comprising one or more sensors, a low power state machine, a comparator, a low power central processing unit (CPU) and a high power CPU. The low power state machine controls the sensor without the intervention of the low power CPU or the high power CPU and the comparator determines whether the output is higher or lower than a predetermined limit, such that the low power CPU processes the sensor output further only if the predetermined limit and conditions of the comparator is met, and does so without the intervention of the high power CPU, and determines based on a pre-configured condition, whether the output value of the processing done by the low power processor should be passed to the high power CPU. The high power CPU may do further processing on the value or data passed by the low power CPU which may be either further processing of the data or formatting for display purposes or alarm generation as a user output.

It would be understood that throughout the description below a first processor refers to a low power microprocessor and a second processor refers to an application or host microprocessor. It would be also understood that the first processed sensor data and the first predetermined threshold limit are always stored in a comparator; and the second processed sensor data and the second predetermined threshold limit are always stored in the first processor or the low power microprocessor.

According to one aspect of the present invention, there is provided an electronic device for measuring and analysing an output signal from at least one sensor, the electronic device comprising:
  a state machine for receiving the output signal from the at least one sensor;
  a comparator operatively coupled with the state machine; and
  a first processor operatively coupled with the comparator;
  wherein the state machine is configured to receive the output signal from the at least one sensor to obtain sensor measurement data and configured to pass the obtained sensor measurement data to the comparator;
  wherein the comparator is configured to process the obtained sensor measurement data into first processed sensor data, and configured to compare the first processed sensor data with a first predetermined threshold limit; and
  wherein the comparator is configured to inform the first processor about the obtained sensor measurement data if the first processed sensor data exceed the first predetermined threshold limit.

Here the first processed sensor data can be more or less than the first predetermined threshold limit so that the comparator informs (or alert) the first processor about the actual sensor measurement data.

The state machine may comprise a low power digital circuit in which a sequence of actions is controlled by input information and a low power timer. The state machine may be configured to provide a standby mode of the electronic device. The state machine may be configured to store the obtained sensor measurement data in a memory for processing. The state machine may be configured to control the obtained sensor measurement data without an intervention of the first processor.

The comparator is configured to determine a difference between the obtained sensor measurement data and a stored sensor measurement data to result in the first processed sensor data. It is possible that the first processed sensor data include other types of data analysis of the obtained sensor measurement data.

The stored sensor measurement data and the first predetermined threshold limit may be stored in a memory of the comparator.

The stored sensor measurement data may comprise a previously measured sensor data or an average of previously measured sensor data.

The first predetermined threshold limit may comprise a high threshold value and a low threshold value.

The comparator may be configured to inform the first processor if the obtained sensor measurement data are higher than the stored sensor measurement data by more than the high threshold value.

The comparator may be configured to inform the first processor if the obtained sensor measurement data are smaller than the stored sensor measurement data by less than the low threshold value.

The comparator may be configured to add new sensor measurement data from the state machine to the stored sensor measurement data of the comparator.

The comparator may be configured to pass the obtained sensor measurement data to the first processor.

The comparator may comprise a digital hardware block to compare digital numbers, or a circuit arrangement that compares analogue values or a combination of digital and analogue circuitry.

The electronic device may further comprise a second processor operatively coupled with the first processor.

The first predetermined threshold limit stored in the comparator may be set by any one of the first processor and the second processor.

The first processor may be configured to process the obtained sensor measurement data into second processed sensor data by performing a set of calculations on the obtained sensor measurement data.

The first processor may be configured to compare the second processed sensor data with a second predetermined threshold limit. The second predetermined threshold limit may be stored in a memory of the first processor.

The first processor may be configured to inform the second processor about the second processed sensor data if the second processed sensor data exceed the second predetermined threshold limit.

The first processor may be configured to pass the second processed sensor data to the second processor for further processing if the second processed sensor data exceed the second predetermined threshold limit.

The second processor is configured to format the second processed sensor data for displaying to a user, or for generating an alarm to the user.

The second processor may be configured to consume more power than the first processor.

The first processor may be a low power microprocessor. The second processor may be an application processor which is configured to perform high power processing. The applications processor may be within a portable handheld device According to the embodiments of the invention, there is provided an electronic assembly comprising at least one sensor and the electronic device as described above.

The at least one sensor may be a gas sensor comprising a heater, sensing electrodes and a gas sensitive layer formed on the sensing electrodes.

The state machine may be configured to apply a voltage across the heater for a predetermined time and configured to measure a resistance value of the gas sensitive layer at a further predetermined time. The resistance value of the gas sensitive layer may be the sensor measurement data.

The comparator may be configured to pass the resistance value from the gas sensor to the first processor if the difference between the resistance value and a stored sensor measurement data comprising a stored resistance value exceeds the first predetermined threshold limit.

The first processor may be configured to process the resistance value from the gas sensor into a gas concentration value by performing a set of calculations on the resistance value of the gas sensor.

The first processor may be configured to pass the gas concentration value to the second processor if the gas concentration value in the first processor exceeds a second predetermined threshold limit stored in the first processor.

The second processor may be configured to format the gas concentration value for displaying to a user, or for generating an alarm to the user.

The at least one electronic sensor may be a humidity sensor or a pressure sensor.

The electronic assembly may be an integrated device comprising said at least one sensor and a silicon integrated circuit on a single device.

The electronic assembly may comprise two devices in one package, wherein one device is a sensor and the second device is a silicon integrated circuit.

According to a further aspect of the present invention, there is provided a method for controlling power distribution in an electronic device, the electronic device comprising: a state machine for receiving the output signal from the at least one sensor; a comparator operatively coupled with the state machine; and a first processor operatively coupled with the comparator;

the method comprising:
receiving at the state machine the output signal from the at least one sensor to obtain sensor measurement data,
passing the obtained sensor measurement data from the state machine to the comparator;
processing at the comparator the obtained sensor measurement data into first processed sensor data,
comparing at the comparator the first processed sensor data with a first predetermined threshold limit; and
informing the first processor about the obtained sensor measurement data by the comparator if the first processed sensor data exceed the first predetermined threshold limit.

The method may further comprise, at the comparator, determining a difference between the obtained sensor measurement data and a stored sensor measurement data to result in the first processed sensor data.

The stored sensor measurement data may comprise a previously measured sensor data or an average of previously measured sensor data.

The first predetermined threshold limit may comprise a high threshold value and a low threshold value.

The method may further comprise informing the first processor by the comparator if the obtained sensor measurement data are higher than the stored sensor measurement data by more than the high threshold value.

The method may further comprise informing the first processor by the comparator if the obtained sensor measurement data are smaller than the stored sensor measurement data by less than the low threshold value.

The method may further comprise comprising passing the obtained sensor measurement data to the first processor.

The electronic device may further comprise a second processor operatively coupled with the first processor.

The method may further comprise processing at the first processor the obtained sensor measurement data into second processed sensor data by performing a set of calculations on the obtained sensor measurement data.

The method may further comprise comparing at the first processor the second processed sensor data with a second predetermined threshold limit.

The method may further comprise passing the second processed sensor data from the first processor to the second processor for further processing if the second processed sensor data in the first processor exceed the second predetermined threshold limit.

The method may further comprise formatting at the second processor the second processed sensor data for displaying to a user, or for generating an alarm to the user.

BRIEF DESCRIPTION OF THE PREFERRED EMBODIMENTS

Some preferred embodiments of the invention will now be described by way of example only and with reference to the accompanying drawings, in which.

DETAILED DESCRIPTION OF THE PREFERRED EMBODIMENTS

Figure 1:
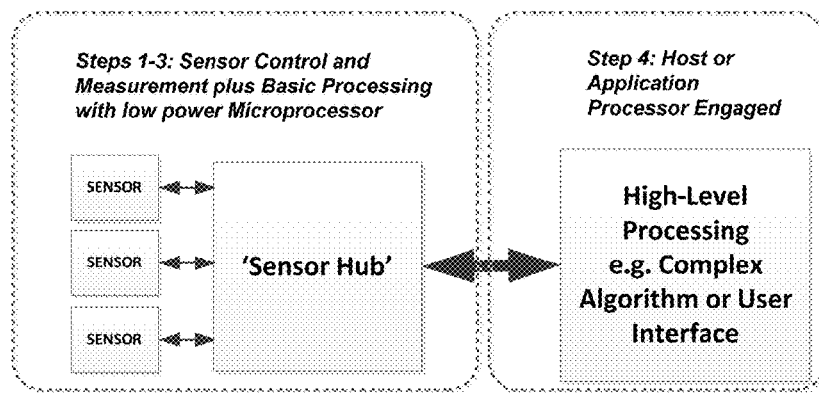
FIG. 1 illustrates a prior art sensor hub architecture.
Figure 2:
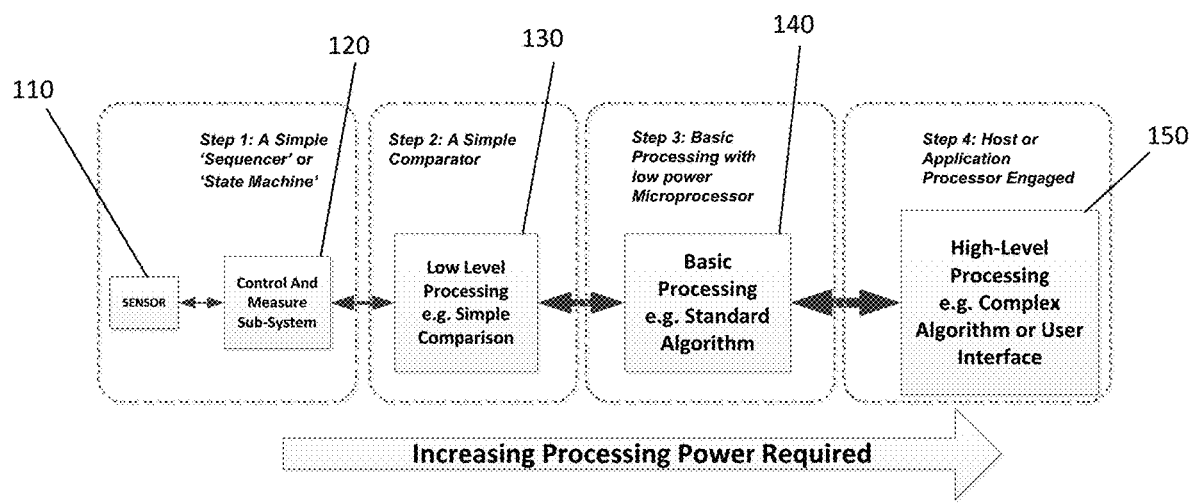
FIG. 2 illustrates a block diagram of an electronic device according to one embodiment of the present invention.

FIG. 2 illustrates a block diagram of an electronic device according to one embodiment of the present invention. The block diagram also illustrates functional steps of the electronic device. The electronic device includes a state machine 120 which is capable of obtaining output signals from one or more sensors 110. The electronic device also includes a comparator 130 for low level processing and a low level processing microprocessor (or the first processor) 140, both being coupled with one another. The electronic device also includes a high level processing microprocessor or the host or application processor (or the second processor) 150 which is operatively coupled with the low level microprocessor 140.

It would be appreciated that the electronic device can be a part of an electronic assembly which includes one or more sensors 110 and the electronic device. The electronic assembly could then be a part of portable device such as a mobile phone, tablet, etc. In other embodiments, the electronic device itself can include the sensors 110, the state machine 120, the comparator 130, the low level processor 140 and the high level processor 150. These components can be all integrated within the electronic device. In other embodiments, the electronic device or assembly comprises two devices in one package, in which one device is a sensor and the second device is a silicon integrated circuit.

Embodiments of the invention describe methods by which the electronic device for the low power system can have a hierarchical approach, using the minimum resources appropriate to the task:

Using a simple 'sequencer' or 'state machine' 120 using a low power timer to control inputs and record outputs. Such a 'sequencer' or 'state machine' 120 may, for example, assert a voltage across the heater (or an equivalent pulse-width modulated voltage) for a specified time and measure the voltage across a biased metal oxide sensor element at a specific time, using a timer or counter, without the need of a microprocessor.

Using a configurable comparator 130 to determine whether a change in conditions (e.g. variation in measurement results) has occurred and make an escalation judgement if the change should generate an alert and/or interrupt to a microprocessor for further processing or confirmation. Such a comparator 130 may, for example, determine whether the most recent measurement (e.g. the voltage across a biased metal oxide sensor element) is significantly bigger or smaller than previous measurements (or stored measurements in the comparator). This difference may be set, perhaps with multiple measurements averaged, to prevent measurement inaccuracies or trivial changes from triggering the alert and/or interrupt. If the difference (or the first processed sensor data) between the most recent measurement value and the stored measurement value is significantly more than a predetermined or pre-configured high threshold limit (the first threshold limit), or significantly less than a predetermined low threshold (the first threshold limit), then the comparator 130 at least informs (or alert or interrupt) the low level processor about the most recent measurement value. The comparator 130 can eventually pass the most recent measurement value to the low level processor 140. Broadly speaking, the comparator 130 processes the most recent measurement data and then compare the processed data with the first threshold limit to decide whether or not the most recent measurement value should be informed to the low level processor. It would be appreciated that the function of the comparator 130 described above may be related to a gas sensor measurement. The operation of the comparator may be different for other types of sensors.

Using a low power microprocessor (or the first processor) 140 to process the raw data to determine the sensor reading (or the most recent measurement data, which may be the resistance values of a sensitive layer of a gas sensor), and make an escalation judgement if the change should generate an alert and/or interrupt to the Host or Applications Processor (or a second processor) 150 for further processing or confirmation. Low power microprocessors 140 can apply simple algorithms or calculations on the measurements taken to determine the significance of any measurement changes using much less power than the larger processors that are typically used as Host or Applications Processors 150. Thus the low level processor 140 converts the raw measurement data into a processed sensor data (or the second processed sensor data). For example, for a gas sensor, the low level processor 140 processes the resistance values (or the raw measurement data) into a gas concentration values by using the simple algorithm or calculations. If the processed data (e.g. the gas concentration values) is significantly higher than a further threshold limit (the second threshold limit) stored in the low level processor 140, then the low level processor 140 passes the processed data (e.g. the gas concentration values) to the host processors 150. The Host or Applications Processors 150 generally have resources that take more power, but would enable additional processing to be done using more complicated algorithms, if necessary.

The Host or Applications Processor 150 has the processed sensor reading but only be activated for a short time to receive the data and use it in any higher level application (APP), which could involve further processing and/or provide the processed data to the user.

In one embodiment, simple control and measurement of a chemical gas sensor is achieved by applying a voltage across a heater element for a pre-determined time and then measuring the resistance of the sensor element. This can be achieved by simple logic and low-power timers of the state machine 120 that can place all circuitry in a low power 'standby' state when not needed. This simple logic (or the state machine) 120 can store the sensor measurement in a register for processing.

Broadly speaking, the simplest level of processing is to compare the new level with previous measured levels. This can be done with a simple comparison (by the comparator 130) and if no change is detected, or the change is small and below a pre-set threshold no further processing is required and higher power processing need not be used.

If the comparator 130 detects a change and/or the change is beyond a threshold limit (or the first threshold limit) then it can inform a more capable processing level, for example the low level processor 140. This next processing level can process the data with an algorithm or algorithms that can determine whether the newly-detected level is significant or not. If it is not significant the simple comparator stage can be reconfigured and then no further action is required and higher power processing need not be used. If the level or change is deemed significant, further processing can be done at this level or a higher level—host or application processor 150—can be informed with an alert message or an interrupt.

The Host or Application Processor 150 can then determine the action to take, which could involve further processing, data logging and initiating user interactions via visible or audible means. This highest power processing, requiring the highest load on any power supply is thus only used when necessary.

Figure 3:
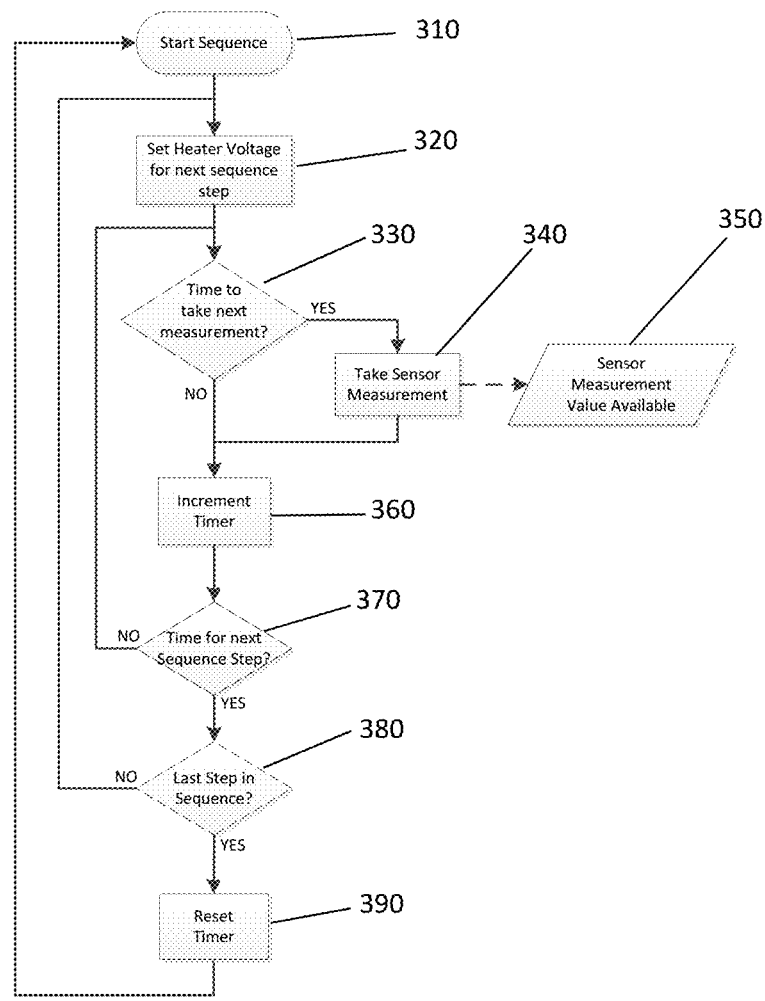
FIG. 3 illustrates a flow diagram describing the steps performed by the state machine of FIG. 2.

FIG. 3 illustrates a flow diagram describing the steps performed by the state machine of FIG. 2. The steps can be implemented in a simple digital hardware (e.g. in the state machine 120) to provide a low power solution that does not need to use a microprocessor. The steps are described as follows:

In step 310, the state machine 120 starts a sequence of operation.

In step 320, the state machine sets the heater voltage for next sequence step.

In step 330, the state machine determines if it is time to take next measurement. If yes, in step 340, it takes the next sensor measurement and in step 350, it makes the sensor measurement value available. If no, in step 360, it increments the timer.

In step 370, the state machine determines if it is the time for next sequence step. If no, then it goes back to step 330. If yes, in step 380, it determines whether the last step in sequence. If no, it goes back to step 320. If yes, in step 390, it resets the timer and goes back to step 310.

Figure 4:
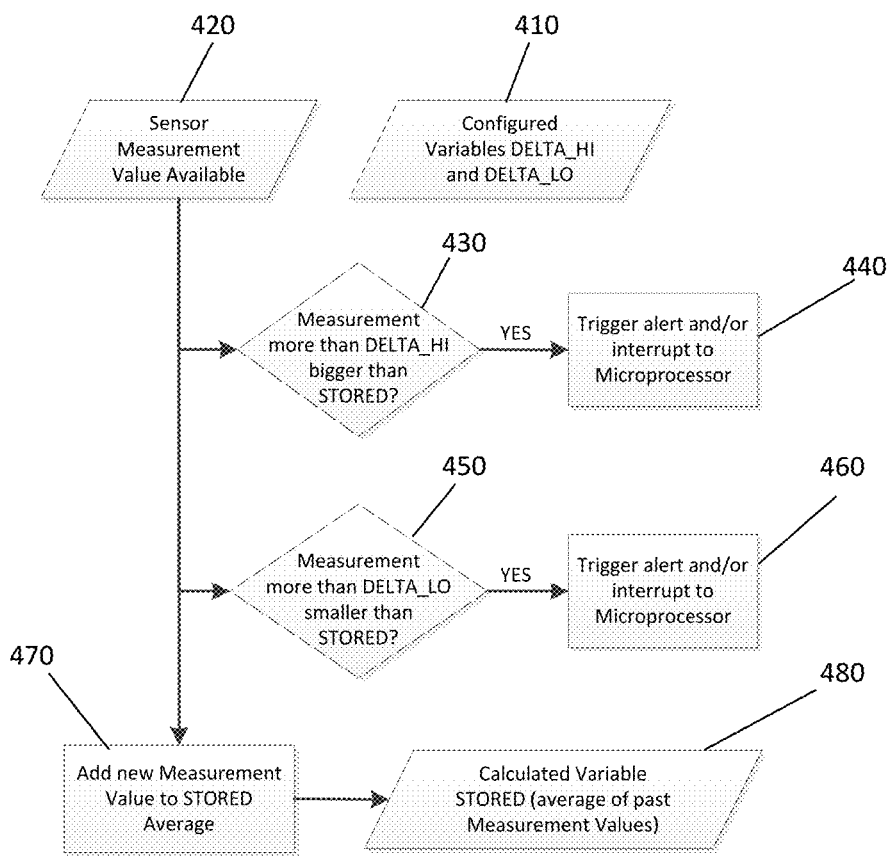
FIG. 4 illustrates a flow diagram describing the steps performed by the comparator of FIG. 2.

FIG. 4 illustrates a flow diagram describing the steps performed by the comparator of FIG. 2. The steps can be implemented in a simple digital hardware (e.g. in the comparator 130) to provide a low power solution that does not need to use a microprocessor. The steps are described as follows:

In step 410, the comparator set high threshold values and low threshold values in the memory of the comparator relating to how much the current sensor reading must change from a stored measurement value in order to trigger an alert and/or interrupt, and/or to pass (forward or transmit) the current sensor reading to the low level processor 140. The stored measurement value relates to a previously measured sensor value or an average of a number of previously measured sensor values. The high threshold value relates to a predetermined difference value between the last sensor reading and the stored measurement value. The low threshold value relates to a predetermined difference value between the last sensor reading and the stored measurement value.

In step 420, the comparator receives sensor measurement values from the state machine 130.

In step 430, the comparator compares the sensor measurement values with the stored measurement values in step 410 and if the sensor measurement values are bigger than the stored measurement values by more than the high threshold values and then, in step 440, the comparator triggers alert and/or interrupt to the low level microprocessor 140. For example, the high threshold value can be set to +5 and the difference between the sensor measurement value and the stored measurement value should be more than +5 to trigger the alert to the low level microprocessor 140.

In step 450, the comparator compares the sensor measurement values with the stored measurement values in step 410 and if the sensor measurement values are smaller than the stored measurement values by less than the low threshold values then, in step 460, the comparator triggers alert and/or interrupt to the low level microprocessor 140. For example, the low threshold value can be set to −5 and the difference between the sensor measurement value and the stored measurement value should be less than −5 to trigger the alert to the low level microprocessor 140.

In step 470, the comparator adds new measurement value to stored measurement (average) values.

In step 480, the comparator calculates variable stored values which are the average of pas measurement values.

Although the aforementioned description refers to measurement of gas sensors, it would be appreciated that the above description is not restricted to gas sensors only. The processing steps and techniques described above can also be applicable to other types of sensors such as humidity and/or pressure sensors.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. An electronic device for measuring and analysing an output signal from at least one gas sensor, the electronic device comprising:
   a control and measure sub-system;
   a comparator operatively coupled with the control and measure sub-system; and
   a low power microprocessor operatively coupled with the comparator, wherein the comparator is a digital hardware separate from the low power microprocessor; and
   a second processor operatively coupled with the low power microprocessor, wherein the second processor is a higher power processor than the low power microprocessor and is an application processor configured to perform high power processing;
   wherein the control and measure sub-system uses a low-power timer to control an input to the at least one gas sensor, and receives and records the output signal from the at least one gas sensor to obtain sensor measurement data, and is further configured to pass the obtained sensor measurement data to the comparator, wherein the control and measure sub-system controls the input and records the output signal of the at least one gas sensor without an intervention of any of the low power microprocessor or the second processor;

wherein the comparator is configured to process the obtained sensor measurement data into first processed sensor data, and configured to compare the first processed sensor data with a first predetermined threshold limit, wherein the first processed sensor data and the first predetermined threshold limit are resistance values of the at least one gas sensor;

wherein the comparator is configured to inform the low power microprocessor about the obtained sensor measurement data in response to the first processed sensor data exceeding the first predetermined threshold limit; and wherein the low power microprocessor performs a set of calculations on the obtained sensor measurement data to obtain second processed sensor data, which is a gas concentration value, without intervention of the second processor; and the low power microprocessor is configured to compare the second processed sensor data with a second predetermined threshold limit, wherein the low power microprocessor is configured to pass the second processed sensor data to the second processor for further processing in response to the second processed sensor data in the low power microprocessor exceeding the second predetermined threshold limit.

2. An electronic device according to claim 1, wherein the control and measure sub-system comprises a low power digital circuit in which a sequence of actions is controlled by input information and a low power timer.

3. An electronic device according to claim 1, wherein the control and measure sub-system is configured to provide a standby mode of the electronic device.

4. An electronic device according to claim 1, wherein the control and measure sub-system is configured to store the obtained sensor measurement data in a memory for processing.

5. An electronic device according to claim 1, wherein the comparator is configured to determine a difference between the obtained sensor measurement data and a stored sensor measurement data to result in the first processed sensor data.

6. An electronic device according to claim 5, wherein the stored sensor measurement data and the first predetermined threshold limit are stored in a memory of the comparator.

7. An electronic device according to claim 5, wherein the stored sensor measurement data comprise a previously measured sensor data or an average of previously measured sensor data.

8. An electronic device according to claim 5, wherein the first predetermined threshold limit comprises a high threshold value and a low threshold value.

9. An electronic device according to claim 8, wherein the comparator is configured to inform the low power microprocessor if the obtained sensor measurement data are higher than the stored sensor measurement data by more than the high threshold value.

10. An electronic device according to claim 8, wherein the comparator is configured to inform the low power microprocessor if the obtained sensor measurement data are smaller than the stored sensor measurement data by less than the low threshold value.

11. An electronic device according to claim 5, wherein the comparator is configured to add new sensor measurement data from the control and measure sub-system to the stored sensor measurement data of the comparator.

12. An electronic device according to claim 1, wherein the comparator is configured to pass the obtained sensor measurement data to the low power microprocessor.

13. An electronic device according to claim 1, wherein the comparator comprises a digital hardware block to compare digital numbers, or a circuit arrangement that compares analogue values or a combination of digital and analogue circuitry.

14. An electronic device according to claim 1, wherein the first predetermined threshold limit stored in the comparator is set by any one of the low power microprocessor and the second processor.

15. An electronic device according to claim 1, wherein the second predetermined threshold limit is stored in a memory of the low power microprocessor.

16. An electronic device according to claim 1, wherein the low power microprocessor is configured to inform the second processor about the second processed sensor data if the second processed sensor data exceed the second predetermined threshold limit.

17. An electronic device according to claim 1, wherein the second processor is configured to format the second processed sensor data for displaying to a user, or for generating an alarm to the user.

18. An electronic device according to claim 1, wherein the second processor is configured to consume more power than the low power microprocessor.

19. An electronic assembly comprising:
at least one gas sensor; and
the electronic device according to claim 1.

20. An electronic assembly according to claim 19, wherein the at least one gas sensor is a gas sensor comprising a heater, sensing electrodes and a gas sensitive layer formed on the sensing electrodes.

21. An electronic assembly according to claim 20, wherein the control and measure sub-system is configured to apply a voltage across the heater for a predetermined time and configured to measure a resistance value of the gas sensitive layer at a further predetermined time.

22. An electronic assembly according to claim 21, wherein the resistance value of the gas sensitive layer is the sensor measurement data.

23. An electronic assembly according to claim 22, wherein the comparator is configured to pass the resistance value from the gas sensor to the low power microprocessor if the difference between the resistance value and a stored sensor measurement data comprising a stored resistance value exceeds the first predetermined threshold limit.

24. An electronic assembly according to claim 23, wherein the low power microprocessor is configured to process the resistance value from the gas sensor into a gas concentration value by performing a set of calculations on the resistance value of the gas sensor.

25. An electronic assembly according to claim 24, wherein the low power microprocessor is configured to pass the gas concentration value to the second processor if the gas concentration value in the low power microprocessor exceeds a second predetermined threshold limit stored in the low power microprocessor.

26. An electronic assembly according to claim 25, wherein the second processor is configured to format the gas concentration value for displaying to a user, or for generating an alarm to the user.

27. An electronic assembly according to claim 19, wherein the electronic assembly is an integrated device comprising said at least one gas sensor and a silicon integrated circuit on a single device.

28. An electronic assembly according to claim 19, wherein the electronic assembly comprises two devices in one package, wherein one device is a sensor and the second device is a silicon integrated circuit.

29. A method for controlling power distribution in an electronic device, the electronic device comprising: a control and measure sub-system that receives an output signal from at least one gas sensor; a comparator operatively coupled with the control and measure sub-system; a low power microprocessor operatively coupled with the comparator, and a second processor operatively coupled with the low power microprocessor; wherein the second processor is a higher power processor than the low power microprocessor, and is an application processor configured to perform high power processing;
- wherein the comparator is a digital hardware separate from the low power microprocessor, and wherein the control and measure sub-system uses a low-power timer to control an input to the at least one gas sensor without an intervention of the low power microprocessor;

the method comprising:
- receiving and recording, at the control and measure sub-system, the output signal from the at least one gas sensor to obtain sensor measurement data, passing the obtained sensor measurement data from the control and measure sub-system to the comparator;
- processing at the comparator the obtained sensor measurement data into first processed sensor data,
- comparing at the comparator the first processed sensor data with a first predetermined threshold limit, wherein the first processed sensor data and the first predetermined threshold limit are resistance values of the gas sensor;
- informing the low power microprocessor about the obtained sensor measurement data by the comparator in response to the first processed sensor data exceeding the first predetermined threshold limit; and
- processing at the low power microprocessor the obtained sensor measurement data into second processed sensor data, which is a gas concentration value, by performing a set of calculations on the obtained sensor measurement data, without intervention of the second processor, and comparing the second processed sensor data with a second predetermined threshold limit;
- passing, by the low power microprocessor, the second processed sensor data to the second processor for further processing in response to the second processed sensor data in the low power microprocessor exceeding the second predetermined threshold limit.

30. A method according to claim 29, further comprising, at the comparator, determining a difference between the obtained sensor measurement data and a stored sensor measurement data to result in the first processed sensor data.

31. A method according to claim 30, wherein the stored sensor measurement data comprise a previously measured sensor data or an average of previously measured sensor data.

32. A method according to claim 30, wherein the first predetermined threshold limit comprises a high threshold value and a low threshold value.

33. A method according to claim 32, further comprising informing the low power microprocessor first processor by the comparator if the obtained sensor measurement data are higher than the stored sensor measurement data by more than the high threshold value.

34. A method according to claim 32, further comprising informing the low power microprocessor by the comparator if the obtained sensor measurement data are smaller than the stored sensor measurement data by less than the low threshold value.

35. A method according to claim 29, further comprising passing the obtained sensor measurement data to the low power microprocessor.

36. A method according to claim 29, further comprising comparing at the low power microprocessor the second processed sensor data with a second predetermined threshold limit.

37. A method according to claim 36, further comprising passing the second processed sensor data from the low power microprocessor to the second processor for further processing if the second processed sensor data in the low power microprocessor exceed the second predetermined threshold limit.

38. A method according to claim 37, further comprising formatting at the second processor the second processed sensor data for displaying to a user, or for generating an alarm to the user.

* * * * *